(12) United States Patent
Lemaire et al.

(10) Patent No.: US 10,416,038 B2
(45) Date of Patent: Sep. 17, 2019

(54) METHOD FOR CHECKING A GEOMETRIC CHARACTERISTIC AND AN OPTICAL CHARACTERISTIC OF A TRIMMED OPHTHALMIC LENS AND ASSOCIATED DEVICE

(71) Applicant: ESSILOR INTERNATIONAL (COMPAGNIE GENERALE D'OPTIQUE), Charenton-le-pont (FR)

(72) Inventors: Cedric Lemaire, Charenton-le-Pont (FR); Xavier Lippens, Charenton-le-Pont (FR)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 0 days.

(21) Appl. No.: 15/743,537

(22) PCT Filed: Jul. 28, 2016

(86) PCT No.: PCT/FR2016/051968
§ 371 (c)(1),
(2) Date: Jan. 10, 2018

(87) PCT Pub. No.: WO2017/017385
PCT Pub. Date: Feb. 2, 2017

(65) Prior Publication Data
US 2018/0195931 A1    Jul. 12, 2018

(30) Foreign Application Priority Data

Jul. 30, 2015   (FR) ..................... 15 57327

(51) Int. Cl.
*G01M 11/02*    (2006.01)
*G01B 11/24*    (2006.01)
(Continued)

(52) U.S. Cl.
CPC ......... *G01M 11/0242* (2013.01); *G01B 11/24* (2013.01); *G01M 11/025* (2013.01);
(Continued)

(58) Field of Classification Search
CPC .......... G01M 11/0278; G01M 11/0242; G01N 21/958; G01N 21/887; G01N 2021/8887;
(Continued)

(56) References Cited

U.S. PATENT DOCUMENTS 5,085,276 A * 2/1992 Rivas ..................... E21B 43/26
                                                        166/303
5,828,446 A   10/1998 Davis
(Continued)

FOREIGN PATENT DOCUMENTS

FR    2 710 162 A1    3/1995
FR    2 878 970 A1    6/2006
(Continued)

OTHER PUBLICATIONS

International Search Report, dated Nov. 7, 2016, from corresponding PCT application No. PCT/FR2016/051968.
(Continued)

*Primary Examiner* — Sang H Nguyen
(74) *Attorney, Agent, or Firm* — Young & Thompson

(57) ABSTRACT

Disclosed is a method for checking at least one geometric characteristic and one optical characteristic of a trimmed ophthalmic lens (10) including the following steps: a) arranging the trimmed ophthalmic lens on a support (110), b) capturing at least one image of the trimmed ophthalmic lens, c) determining, from the image, a measured geometric characteristic of the trimmed ophthalmic lens, d) determining at least one measured optical characteristic of the trimmed ophthalmic lens in a reference frame of the image captured in step b), e) comparing the measured geometric
(Continued)

characteristic associated with the measured optical characteristic to a predefined desired ophthalmic lens model, including at least one desired geometric characteristic and one associated desired optical characteristic. Also disclosed is an associated checking device.

20 Claims, 2 Drawing Sheets

(51) Int. Cl.
    *G01N 21/958*     (2006.01)
    *G02C 13/00*     (2006.01)

(52) U.S. Cl.
    CPC .... *G01M 11/0221* (2013.01); *G01M 11/0264* (2013.01); *G01N 21/958* (2013.01); *G02C 13/005* (2013.01); *G01N 2021/9583* (2013.01)

(58) Field of Classification Search
    CPC ... G01N 2021/9583; G01N 2021/9511; G01N 2201/062; G01B 11/24; G02C 13/005
    See application file for complete search history.

(56) References Cited

U.S. PATENT DOCUMENTS

| | | | | |
|---|---|---|---|---|
| 6,154,274 | A * | 11/2000 | Davis | G01M 11/0207 348/127 |
| 6,314,199 | B1 * | 11/2001 | Hofer | G01N 21/88 356/239.2 |
| 7,766,723 | B2 | 8/2010 | Mazoyer | |
| 8,352,065 | B2 * | 1/2013 | Dubois | B24B 1/00 700/182 |
| 2002/0163638 | A1 * | 11/2002 | Biel | G01M 11/0278 356/239.2 |
| 2004/0042003 | A1 * | 3/2004 | Dispenza | G01M 11/0214 356/239.1 |
| 2007/0195311 | A1 * | 8/2007 | Morgan | A61F 2/16 356/124 |
| 2007/0213861 | A1 * | 9/2007 | Takeichi | B23B 41/00 451/240 |
| 2008/0137076 | A1 * | 6/2008 | Clements | B65D 1/30 356/124 |
| 2009/0303465 | A1 * | 12/2009 | Clements | G01M 11/0278 356/124 |
| 2010/0290694 | A1 | 11/2010 | Dubois et al. | |
| 2015/0002656 | A1 * | 1/2015 | Dubois | G01M 11/0207 348/95 |
| 2015/0300912 | A1 * | 10/2015 | Allione | G01M 11/0264 356/124.5 |

FOREIGN PATENT DOCUMENTS

| | | |
|---|---|---|
| FR | 2 893 152 A1 | 5/2007 |
| FR | 2 958 040 A1 | 9/2011 |

OTHER PUBLICATIONS

Chinese Office Action for Application No. 201680044580.1, dated Feb. 3, 2019, with English translation provided.

* cited by examiner

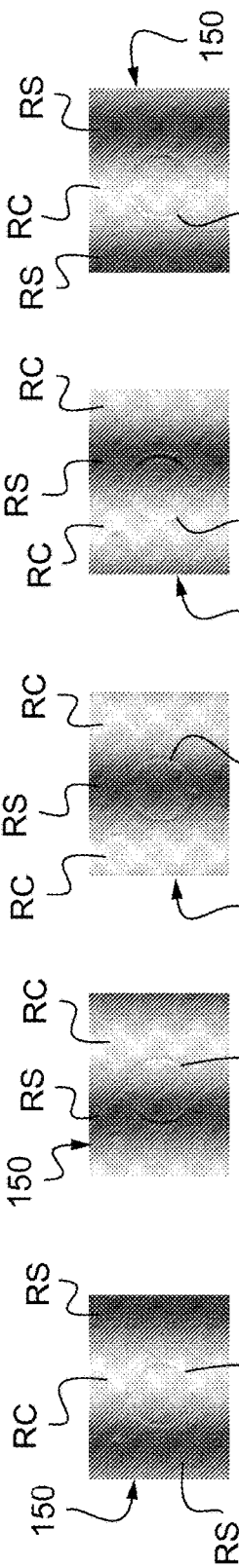
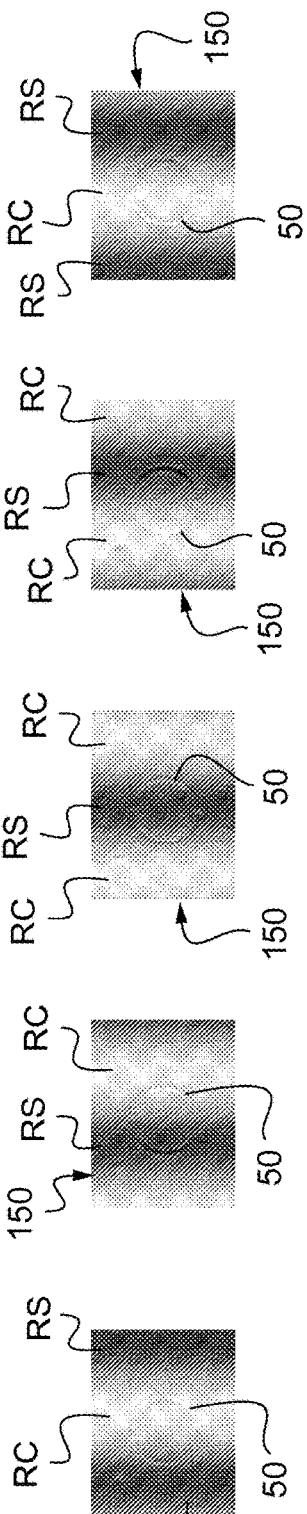
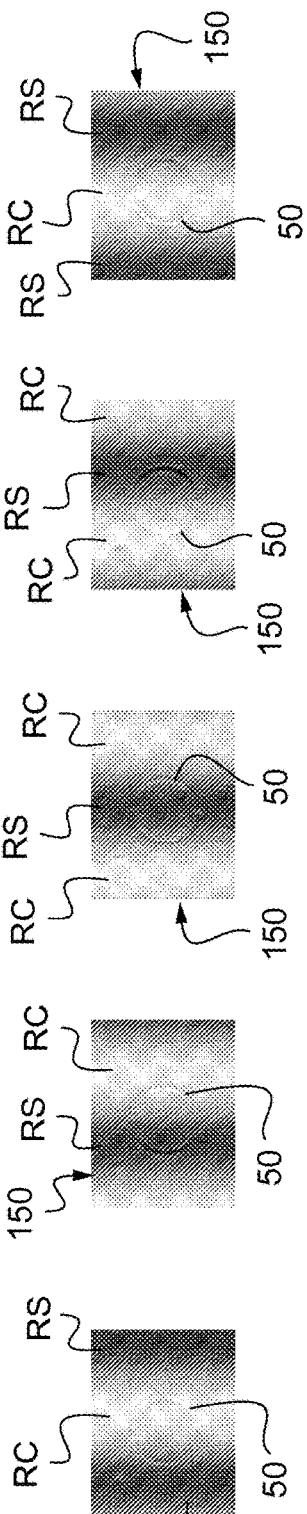
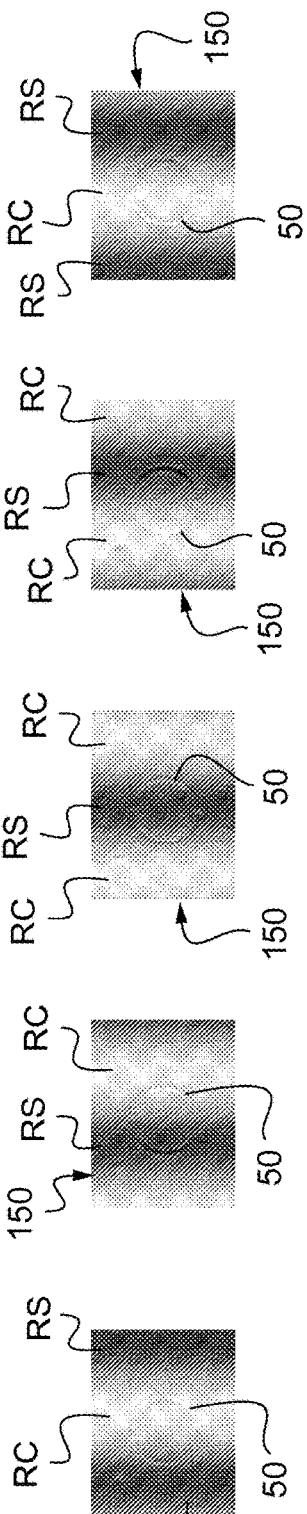
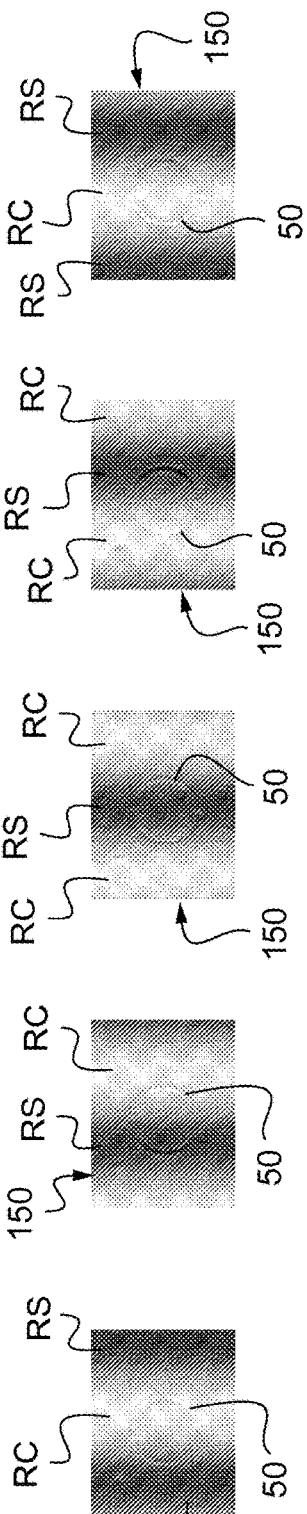
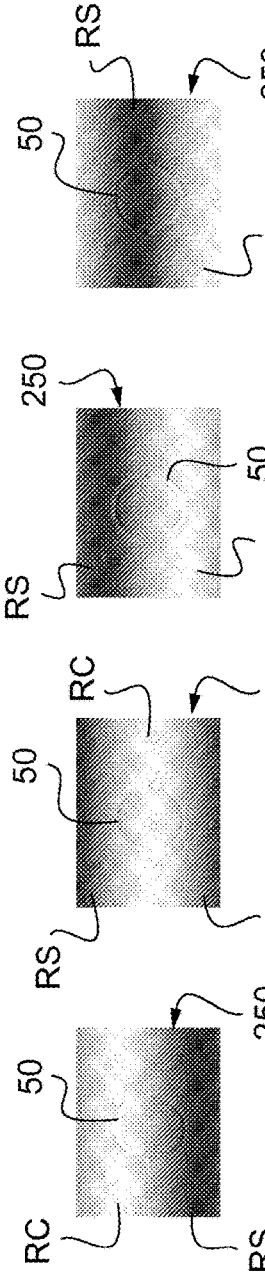
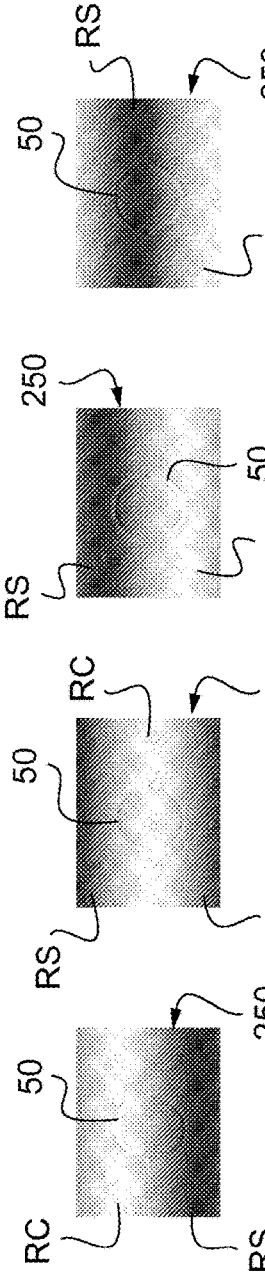
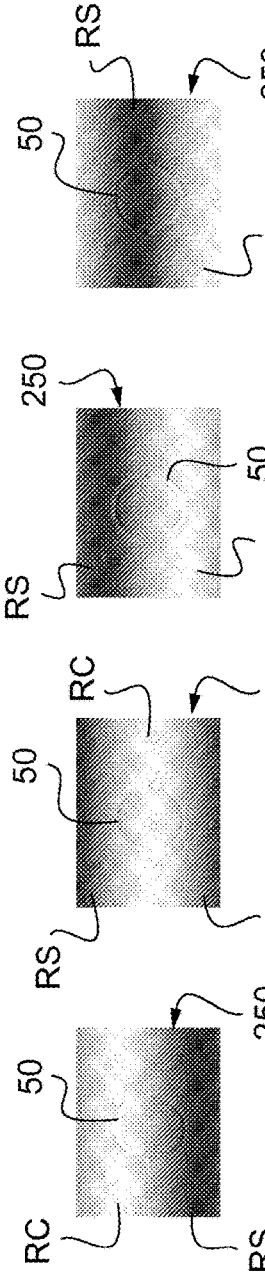
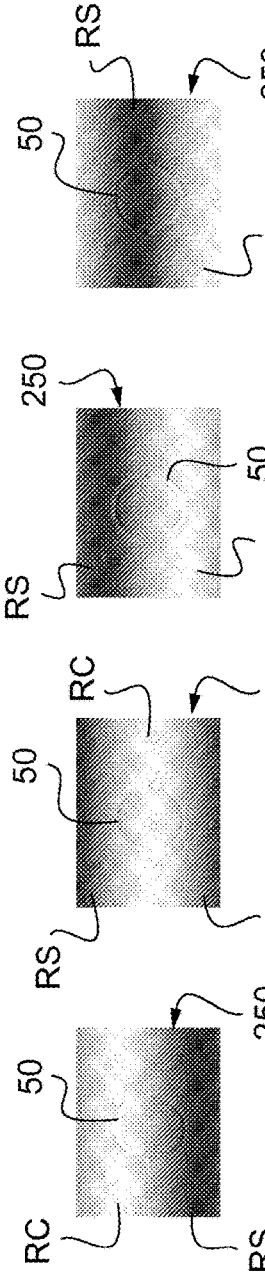
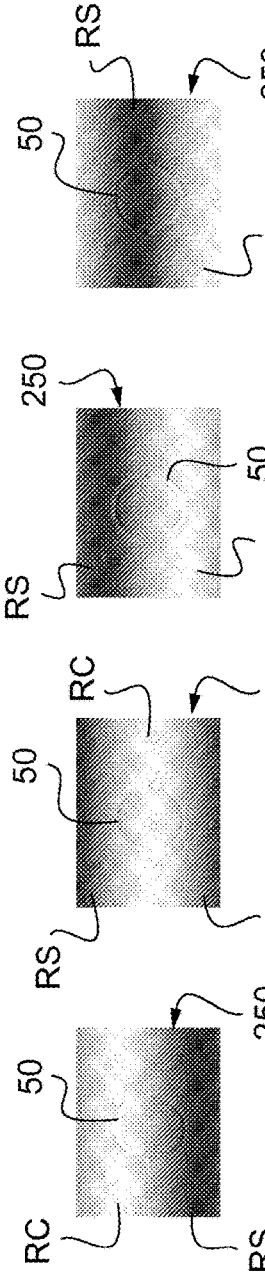
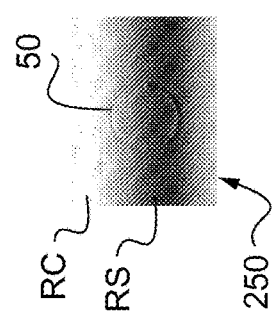
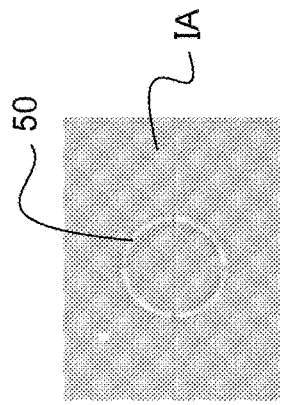

METHOD FOR CHECKING A GEOMETRIC CHARACTERISTIC AND AN OPTICAL CHARACTERISTIC OF A TRIMMED OPHTHALMIC LENS AND ASSOCIATED DEVICE

TECHNICAL FIELD OF THE INVENTION

Generally, the present invention relates to the field of methods for checking edged ophthalmic lenses.

It more particularly relates to a method for checking a geometric characteristic and an optical characteristic of an edged ophthalmic lens.

It also relates to a device for checking at least one geometric and/or optical characteristic of an edged ophthalmic lens.

TECHNOLOGICAL BACKGROUND

Ophthalmic lenses intended to be mounted in a particular spectacle frame are manufactured from an initial circular lens having the optical characteristics required by the prescription of the wearer.

To this end, this initial lens is edged so as to have an outline suitable for the spectacle frame chosen by the wearer, this outline being centered in the initial lens depending on geometrico-morphological characteristics of the wearer, such as interpupillary distance and/or depending on characteristics related to the position of the frame on the face of the wearer, for example the height of the pupils with respect to the lower edge of the frame or the lens in place on the head of the wearer, and/or depending on optical characteristics desired for the edged ophthalmic lens given the prescription of the wearer.

Thus, after the initial lens has been edged, it is known to control the quality of the obtained edged ophthalmic lens, in order to check, on the one hand, that the final outline of the edged ophthalmic lens indeed corresponds to the desired outline depending on the chosen spectacle frame, and, on the other hand, that the optical characteristics of the edged ophthalmic lens indeed correspond to the desired optical characteristics depending on the wearer and the chosen frame.

This quality control is carried out manually and visually, in various steps according to non-standardized protocols. This quality control is thus time-consuming and tedious to carry out. Furthermore, it is imprecise.

SUBJECT OF THE INVENTION

In order to remedy the aforementioned drawbacks of the prior art, the present invention provides a new method for checking a geometric characteristic and an optical characteristic of an edged ophthalmic lens, permitting the quality of edged lenses to be controlled with higher precision and more rapidly.

More particularly, according to the invention such a method is proposed comprising the following steps:
a) the edged ophthalmic lens is placed on a holder,
b) at least one image of this edged ophthalmic lens is captured,
c) on the basis of this image, a measured geometric characteristic of said edged ophthalmic lens is determined,
d) at least one measured optical characteristic of this edged ophthalmic lens is determined in a coordinate system of the image captured in step b),
e) said measured geometric characteristic associated with the measured optical characteristic is compared to a predetermined desired ophthalmic-lens model, comprising at least one corresponding desired geometric characteristic and one corresponding desired optical characteristic.

Thus, by virtue of the checking method according to the invention, it is possible to make the control of the quality of edged ophthalmic lenses automatic and systematic. This quality control is carried out rapidly. The time taken to manufacture ophthalmic lenses is decreased.

Furthermore, the precision of the control of the quality of the geometric characteristics and optical characteristics of the lens is improved.

By virtue of the method according to the invention, the outline and the optical characteristics of the lens may be checked before the ophthalmic lens is mounted in the chosen frame. The quality of the edged ophthalmic lenses sent to the optician for subsequent mounting in the frame is ensured.

Furthermore, by virtue of the method according to the invention, defects in the measured geometric characteristic or measured optical characteristic may be quantified and recorded in order to establish statistical databases on the edged ophthalmic lenses. The traceability of the ophthalmic lenses is improved.

The following are other nonlimiting and advantageous features of the method according to the invention, which may be implemented individually or in any technically possible combination:

in step c), said measured geometric characteristic is the measured outline of the edged ophthalmic lens and, in step e), the desired ophthalmic-lens model comprises a desired outline;

in step d), said optical characteristic comprising the position of the optical center and/or the direction of an optical axis of the edged ophthalmic lens, the following substeps are carried out:

d1) prior to step c), the edged ophthalmic lens is placed in a lensmeter and a mark is made on said edged ophthalmic lens, said mark indicating the optical center and/or the direction of the optical axis on said edged ophthalmic lens, d2) the image of this mark is identified in the image captured in step b);

the holder of said edged ophthalmic lens being located between an image-capturing apparatus suitable for capturing the image of this ophthalmic lens in step b), and a device for displaying a stationary pattern, in step d), by virtue of said image-capturing device, an image of this stationary pattern is captured through the edged ophthalmic lens, and said optical characteristic is determined depending on this image;

the holder of said edged ophthalmic lens being located between an image-capturing apparatus suitable for capturing the image of this ophthalmic lens in step b), and a device for displaying a scrolling pattern, in step d), by virtue of said image-capturing device, a plurality of images of this scrolling pattern are captured through the edged ophthalmic lens, and said optical characteristic is determined depending on this plurality of images;

in step d), the scrolling pattern displayed by the displaying means having a predetermined spatial period and said plurality of images comprising a number m of images, each capture of one image of said plurality of images by the image-capturing device corresponds to the display of the scrolling pattern shifted by a distance equal to $1/m$ times the spatial period of this scrolling pattern with respect to the preceding capture;

in step d), an improved image of said edged ophthalmic lens is determined by applying statistical processing to said plurality of images of the scrolling pattern through the edged ophthalmic lens;

in step d), in said improved image of said edged ophthalmic lens, the image of at least one of the following elements is identified:

engravings produced on the surface of the edged ophthalmic lens or in the volume of the edged ophthalmic lens, the measured outline of the edged ophthalmic lens, an outline of a zone of different optical power to that of the rest of the edged ophthalmic lens, defects in the coating(s) of the edged ophthalmic lens;

said image-capturing device is focused on the holder or on the ophthalmic lens to be edged placed on this holder, at distance from the displaying device;

in step e), said measured geometric characteristic being the measured outline of the edged ophthalmic lens and, in step e), the desired ophthalmic-lens model comprising a desired outline, the following substeps are carried out:
  e1) the measured outline is superposed on the desired outline by minimizing the discrepancy therebetween,
  e2) the discrepancy between the measured optical characteristic and the desired optical characteristic is determined depending on the superposition obtained in step e1);

in step d), said measured optical characteristic of this edged ophthalmic lens comprises at least one of the following characteristics:

measured position of an optical center, measured direction of an optical axis, measured direction of a tint gradient of the edged ophthalmic lens, measured direction of a polarization axis of the edged ophthalmic lens;

in a step f), depending on the comparison made in step e), a parameter relating to the discrepancy between said measured geometric characteristic and said desired geometric characteristic and a parameter relating to the discrepancy between said measured optical characteristic and said desired optical characteristic are determined;

in step f), said parameter relating to the discrepancy between said measured geometric characteristic and said desired geometric characteristic and said parameter relating to the discrepancy between said measured optical characteristic and said desired optical characteristic are compared to tolerance threshold values and, depending on this comparison, an indicator of the conformity of the edged ophthalmic lens is determined;

in a step g), depending on the comparison made in step e), a parameter relating to the discrepancy between said measured optical characteristics is determined for a right lens and a left lens that are intended for said frame; and in step g), said parameter relating to the discrepancy between said measured optical characteristics is compared, for a right lens and a left lens that are intended for said frame, to a tolerance threshold value and, depending on this comparison, an indicator of the conformity of the right and left edged ophthalmic lenses is determined.

The invention also provides a device for checking at least one geometric and/or optical characteristic of an edged ophthalmic lens, comprising:

a holder for said edged lens, on one side of this holder, an image-capturing device, on the other side of this holder, a displaying device suitable for displaying at least one scrolling pattern and for making this scrolling pattern scroll in at least one predetermined scrolling direction with respect to said holder, means for synchronizing a plurality of captures of images by the image-capturing device and the scrolling of the scrolling pattern performed by the displaying device, means for determining said geometric and/or optical characteristic of the edged ophthalmic lens depending on the plurality of captured images and for comparing this geometric and/or optical characteristic with a corresponding desired characteristic.

Advantageously, said scrolling pattern comprises alternating black and white strips and wherein the image-capturing device is focused in proximity to the holder, at distance from said scrolling pattern.

Furthermore, the scrolling pattern displayed by the displaying means having a predetermined spatial period, the synchronizing means are programmed to trigger a number m of image captures, each capture of one image of said plurality of images by the image-capturing device corresponding to the display of the scrolling pattern shifted by a distance equal to 1/m times the spatial period of this pattern with respect to the preceding capture.

DETAILED DESCRIPTION OF AN EXEMPLARY EMBODIMENT

The description which follows with reference to the appended drawings, which are given by way of nonlimiting examples, will make it easy to understand what the invention consists of and how it can be achieved.

In the appended drawings:

FIG. 1 is a schematic view of a checking device according to the invention,

FIG. 2 is a schematic view of the measured outline and measured optical characteristics of an edged ophthalmic lens superposed on the outline desired and optical characteristics desired for this edged ophthalmic lens, FIGS. 3 to 7 are five schematic views of one scrolling pattern seen through the edged ophthalmic lens, this scrolling pattern being shifted by a distance equal to ⅕ times the spatial period of this pattern between each successive figure, in the direction of this spatial period, the pattern here being a vertical line, FIGS. 8 to 12 are five schematic views of another scrolling pattern seen through the edged ophthalmic lens, this scrolling pattern being shifted by a distance equal to ⅕ times the spatial period of this pattern between each successive figure, in the direction of this spatial period, the pattern here being a horizontal line, FIG. 13 is a schematic view of the image obtained by applying statistical processing to images 3 to 7 and/or 8 to 12.

Device

FIG. 1 shows a device 100 for checking at least one geometric and/or optical characteristic of an edged ophthalmic lens 10 according to the invention. This checking device 100 is suitable for implementing the checking method according to the invention.

As FIG. 1 shows, this checking device 100 comprises:

a holder 110 for said edged lens 10, on one side of this holder 110, an image-capturing device 120, on the other side of this holder 110, a displaying device 130 suitable for displaying at least one scrolling pattern 150, 250 and for making this pattern scroll in at least one predetermined scrolling direction with respect to said holder 110, means 140 for synchronizing a plurality of captures of images by the image-capturing device 120 and the scrolling of the scrolling pattern 150, 250 performed by the displaying device 130, means for determining said measured geometric and/or optical characteristic of the edged lens 10 depending on the plurality of captured images and for comparing this measured geometric and/or optical characteristic with a corresponding desired geometric and/or optical characteristic.

More precisely, here, the holder 110 comprises a plate made of transparent material, for example made of glass or of transparent plastic.

The holder 110 is here intended to receive the edged ophthalmic lens alone.

The edged lens 10 is for example placed directly on this plate, with its back face 11 oriented toward the holder 110 and its front face 12 oriented toward the image-capturing device 120.

As a variant, the holder is intended to receive the edged ophthalmic lens to which a blocking pad is fastened.

Specifically, provision may be made for the holder to also comprise a blocking pad fastened to the front face of the edged lens and for the plate to comprise means for receiving this blocking pad. The blocking pad is preferably the pad used to block the lens during its edging. The edged ophthalmic lens is then oriented with its front face toward the holder and its back face toward the image-capturing device.

Thus, advantageously, the edged lens is replaced in the coordinate system used for the edging. Furthermore, in this way, the images of the edged lens captured subsequently are not subject to deformation due to an undesired inclination of the mean edging plane of the lens with respect to the plane of image capture.

In yet another variant, the holder is intended to receive the edged ophthalmic lens mounted in a spectacle frame.

It is then possible to envision that the edged lens will be mounted in the frame chosen by the wearer and that the holder will comprise means for fastening the pair of spectacles comprising this frame and the edged lenses mounted in this frame.

The checks may then advantageously be carried out on the lens in place in the spectacle frame.

The holder may also be able to simultaneously accommodate the two lenses edged for a given frame. The field of the image-capturing device must then be large enough to simultaneously capture an image of the two edged lenses placed on the holder.

The holder 110 is preferably equipped with a scale marker allowing the scale factor of the images to be deduced from the image of this scale marker identified in an image captured by the image-capturing device.

The image-capturing device 120 is for example a digital camera or a digital video camera.

This image-capturing device 120 is placed on the side of the holder 110 that accommodates the edged lens 10.

A lens or an optical system may be provided between the image-capturing device and the edged lens 10 held by the holder 110 so as to make the device 100 telecentric. The image captured by the image-capturing device then depends little on the height of the edged lens 10 with respect to the holder 110.

The displaying device 130 for example comprises a screen suitable for displaying said scrolling pattern 150, 250. It is preferably a digital screen.

Thus, the displaying device 130 is for example a backlit LCD screen that furthermore plays the role of light source of the device 100. This LCD screen is then suitable for making this scrolling pattern 150, 250 scroll in said predetermined scrolling direction with respect to said holder 110.

The scrolling pattern 150, 250 for example comprises at least one dark strip RS flanked by two lighter strips RC or one light strip RC flanked by two darker strips RS. It preferably comprises a plurality of alternating dark strips RS and light strips RC (see FIGS. 3 to 12). Each strip extends along a longitudinal axis.

The light and dark strips displayed on the digital screen are preferably white and black strips. In other words, the light strips have a uniform display brightness close to 255 and the dark strips have a uniform display brightness close to 0, in RGB value. They preferably have identical widths. They preferably also have substantially straight and parallel edges.

Since the image-capturing device 120 is focused on the holder 110 or on the edged lens 10 placed above, at distance from the display screen 130, the black and white strips of the pattern are blurred and the variation in the brightness of the scrolling pattern 150, 250 seen through the edged lens 10 thus appears continuous.

More precisely, the device 100 is preferably arranged such that the variation in the brightness of the scrolling pattern varies continuously from white to black with a substantially sinusoidal variation.

In other words, in the image captured by the image-capturing device 120, the scrolling pattern 150, 250 has a brightness that continuously varies between two extreme values in a substantially sinusoidal way, one of the two extreme values being close to 0 and the other close to 255, in RGB values.

FIGS. 3 to 7 show a first type of scrolling pattern 150, comprising alternating black and white strips extending along a vertical axis in the plane of image capture.

FIGS. 8 to 12 show a second type of scrolling pattern 250, comprising alternating black and white strips extending along a horizontal axis in the plane of image capture, i.e. in a direction orthogonal to the direction of the strips of the first type of scrolling pattern 150.

Figure 1:
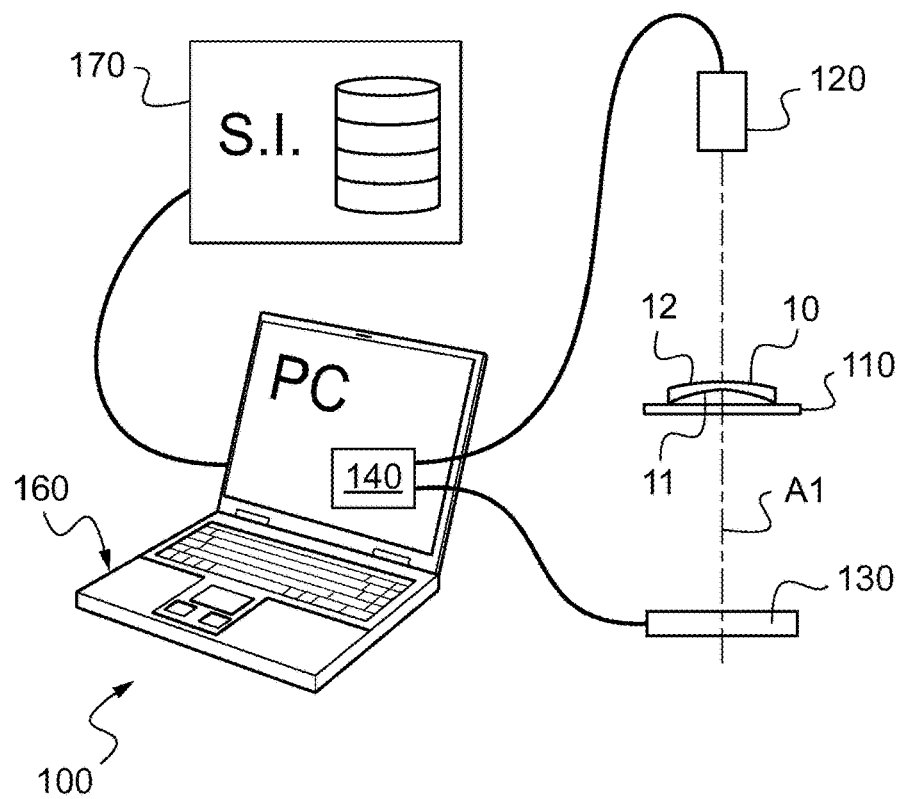

Whatever the scrolling pattern in question, the scrolling direction in which the displaying device 130 is suitable for making the alternating black and white strips scroll is perpendicular to the longitudinal axis along which the strips extend.

In other words, the vertical strips scroll horizontally and the horizontal strips scroll vertically, this being shown in FIGS. 3 to 7 on the one hand and 8 to 12 on the other hand.

The displaying device 130 is also preferably suitable for displaying one or more stationary patterns, for example a Hartmann matrix.

Optionally, the device 100 may also comprise an additional element for displaying a stationary pattern, for example, a Hartmann matrix. It may for example be a transparent LCD screen that is not backlit.

This additional displaying element is then placed between the holder 110 and the displaying device 130.

Of course, the various optical elements of this device 100, namely the image-capturing device 120, the holder 110 and the displaying device 130, and, where appropriate, optional optical elements such as the telecentering optical system or lens and the additional element for displaying a stationary pattern, are centered on a common optical axis A1 (FIG. 1) of the device 100.

The device 100 lastly comprises electronic and computational means, here taking the form of a computer 160, programmed:
- to trigger the capture of each image of the edged lens depending on the scrolling motion of the pattern 150, 250 and
- to determine the geometric and/or optical characteristics of the edged lens 10 sought depending on the plurality of captured images and to compare this geometric and/or optical characteristic with a corresponding desired characteristic.

To this end, the computer 160 in particular comprises said means 140 for synchronizing the plurality of captures of images by the image-capturing device 120 and the scrolling of the pattern 150, 250 performed by the displaying device 130 and said determining means.

Said electronic and computational means furthermore here comprise a database 170 (FIG. 1) which the computer 160 may access in order to read certain information or to save certain results.

Method

This device 100 allows the method for checking the outline and an optical characteristic of an edged ophthalmic lens according to the invention to be implemented.

This method comprises the following steps:
a) the edged ophthalmic lens is placed on the holder 110,
b) at least one image of this edged ophthalmic lens is captured using the image-capturing device 120,
c) on the basis of this image, a measured geometric characteristic of said edged ophthalmic lens 10 is determined,
d) at least one measured optical characteristic of this edged ophthalmic lens 10 is determined in a coordinate system of the image captured in step b),
e) said measured geometric characteristic and the measured optical characteristic are compared to a predetermined desired ophthalmic-lens model, comprising at least one desired geometric characteristic and one corresponding desired optical characteristic.

In practice, before the edged lens 10 is checked, the operator obtains information regarding the desired lens.

More precisely, for example, each edged lens 10 is associated with an identifier allowing the geometric and optical characteristics desired for the edged lens to be consulted.

This identifier is called the "job ticket". The operator indicates the number of the job ticket to the computer 160, using the numeric keyboard or using a reader by scanning a barcode of the job ticket. This number allows the computer to access a file associated with the edged lens 10, which file is stored in the database 170 (FIG. 1).

This file contains the geometric and optical characteristics desired for the edged lens 10, in particular:
- a desired outline,
- desired powers,
- the desired orientations of the axes,
- a desired position of the optical center,
- a desired value of the monocular pupillary distance,
- a desired value of the height of the pupil with respect to the lower edge of the edged lens, i.e. the height of the optical center of the edged lens with respect to the lower edge of the edged lens.

Below, edged lenses are classed into three different types: unifocal lenses, having the same power over all their area, bi or trifocal lenses, comprising a body having a first optical power and one or two zones having second and/or third optical powers different from the first, progressive lenses, having an optical power that varies continuously between a far-vision zone and a near-vision zone.

Whatever the type of edged lens, steps a), b) and c) may be carried out in the same way.

The operator places the edged lens 10 to be checked on the holder 110.

He ensures that the edged lens is substantially centered on the holder 110 so that it is in the field of image capture of the image-capturing device 120.

The operator triggers the capture of at least one first image of this edged ophthalmic lens 10.

For the capture of this first image, the LCD screen forming the displaying device 130 is turned on but displays no pattern. The display screen then has a uniform brightness. It is for example entirely white.

The captured image is transferred to the computer 160, which processes the image so as to determine, on the basis of this image, the one or more measured geometric characteristics of the edged lens 10, for example a measured outline 20 of said edged ophthalmic lens 10. This measured outline 20 is determined in the plane of image capture.

As a variant, the measured geometric characteristic of the edged lens determined in step c) may be the relative position of two or three predetermined particular points of the edged lens. It may also be one or more measurements of characteristic distances of this edged lens.

In step d), said measured optical characteristic of this edged ophthalmic lens 10 comprises at least one of the following characteristics:
- measured position of a measured optical center,
- measured direction of a measured optical axis,
- measured direction of a tint gradient of the edged ophthalmic lens 10,
- measured direction of a polarization axis of the edged ophthalmic lens 10.

Step d) is carried out in various ways depending on the type of edged lens 10 in question.

When the edged lens 10 is a unifocal lens, in a first embodiment of step d), the operator or the computer 160 automatically triggers at least one second capture of an image of the edged lens 10, while displaying behind this edged lens 10, with respect to the image-capturing device, the stationary pattern, which for example is the Hartmann matrix.

Thus, in step d), the second image captured by virtue of said image-capturing device is the image of the stationary pattern consisting of the Hartmann matrix through the edged ophthalmic lens 10, and said optical characteristic is determined depending on this second image.

This Hartmann matrix is a matrix of dots the relative positions of which are known in the plane of display of the matrix.

This Hartmann matrix may here be displayed by the displaying device 130. It then constitutes one of the patterns that this device is suitable for displaying.

In practice here the Hartmann matrix is then displayed on the LCD screen of the displaying device 130.

As a variant, the Hartmann matrix may also be displayed on the aforementioned additional displaying element.

This second image is processed by the computer 160, which identifies the dots of the matrix in the second captured image and compares their relative positions in this second image to their relative positions in the plane of display of the matrix.

In the case where the Hartmann matrix is displayed on the LCD screen of the displaying device 130, the processing of the image is modified to take into account the fact that this screen is out of focus.

The computer 160 is also programmed to then determine, depending on the deviation of the dots of the Hartmann matrix in the image of the matrix captured through the edged lens with respect to the position of the dots of this known matrix, the optical center of the edged lens 10 and an optical axis of the lens which is in practice here the cylinder axis (if it exists).

The position of the dots of this matrix is for example determined in the device 100 unloaded via an image captured with no lens placed on the holder 110. These measured optical characteristics (position of the optical center, orientation of the cylinder axis) of the edged ophthalmic lens are thus determined in the coordinate system of the second captured image, which is identical to the coordinate system of the first image captured in step b).

According to a second embodiment of step d) in the case of a unifocal edged lens, in a step d1) prior to step a), the edged ophthalmic lens is placed in a lensmeter and a mark is made on said edged ophthalmic lens, said mark indicating the optical center and/or the optical axis on said ophthalmic lens, and in a step d2) the image of this mark is identified in said first image captured in step b).

In practice, the lensmeter allows 3 dots representing the optical center and the direction of the cylinder axis to be marked on the front face of the edged lens, these dots being easily identifiable by image processing.

The measured optical characteristics of the edged ophthalmic lens are here obtained directly in the coordinate system of the first image captured in step b).

When the edged lens 10 is a progressive lens, in step d), by virtue of said image-capturing device 120, a plurality of images of the scrolling pattern 150, 250 displayed on said displaying device 130 are captured through the edged ophthalmic lens 10 and said optical characteristic is determined depending on this plurality of images.

Two examples of pluralities of captured images are shown in FIGS. 3 to 7 and 8 to 12, respectively. Below, the plurality of images shown in FIGS. 3 to 7 will be called the first series of images and the plurality of images shown in FIGS. 8 to 12 will be called the second series of images. Each plurality of images comprises a number m of images, here 5 images.

Generally, the scrolling pattern 150, 250 displayed by the displaying means 130 has a predetermined spatial period.

In the examples of scrolling patterns 150, 250 shown in FIGS. 3 to 7 and 8 to 12, the scrolling pattern 150, 250 comprises alternating black and white strips of the same width, as described above.

The spatial period of each scrolling pattern 150, 250 is equal to the sum of the widths of a black strip and a white strip, i.e. here two times the width of one strip.

Each image capture of said plurality of images counting m images by the image-capturing device 130 then preferably corresponds to the display of the scrolling pattern 150, 250 shifted by a distance equal to 1/m times the spatial period of this scrolling pattern 150, 250 with respect to the preceding capture.

In the examples shown in FIGS. 3 to 7 and 8 to 12, each of the first and second series of images counts 5 images, each image therefore corresponds to the display of the scrolling pattern 150, 250 shifted by ⅕ times the spatial period of this scrolling pattern 150, 250.

Said synchronizing means of the computer 160 are programmed to synchronize the capture of each image of said plurality of images by the image-capturing device 120 and the scrolling of the scrolling pattern 150, 250 performed by the displaying device 130 so as to trigger a number m of image captures, the scrolling pattern 150, 250 being shifted by a distance equal to 1/m times the spatial period of this scrolling pattern 150, 250, in the scrolling direction, between two successive image captures.

Once the m images of a series of images have been captured, these images are transmitted to the computer 160, which is programmed to apply statistical processing to these images.

More precisely, in step d), the computer 160 is here programmed to determine an improved image IA of said edged ophthalmic lens 10 by applying statistical processing to said captured plurality of images of the scrolling pattern 150, 250.

In practice, here, said improved image IA is determined on the basis of the calculation of the standard deviation of said plurality of images from the scrolling pattern 150, 250.

As a variant, said improved image may be determined via other statistical calculations, such as for example the calculation of the variance of the plurality of captured images or the calculation of the maximum or the minimum of each pixel in the plurality of captured images.

In this improved image IA, the scrolling pattern 150, 250 is invisible. The statistical processing thus has the effect of making the scrolling pattern 150, 250 disappear.

Furthermore, in the improved image IA, the outline of phase objects such as micro-engravings on the surface or in the bulk of the edged lens appear clearly.

Thus, in the improved image, it is possible to precisely identify the image of micro-engravings of the edged lens, which conventionally indicate the optical center or the prism reference point, usually denoted PRP, and the direction of the axes of this edged ophthalmic lens.

FIG. 13 for example shows one such micro-engraving 50 of circular shape allowing the position of the optical center, or of the prism reference point PRP, of the edged lens 10 to be determined in the improved image IA.

It will be noted that this micro-engraving 50 is much more clearly visible in the improved image than in the images captured by the image-capturing device 120 shown in FIGS. 3 to 12.

The computer 160 is thus programmed to identify, in said improved image IA of said edged ophthalmic lens 10, at least one of said micro-engravings, and to deduce therefrom the one or more sought optical characteristics, in particular the measured position of the optical center and/or the measured direction of the cylinder axis of the edged lens 10.

When the edged lens 10 is bi or trifocal, it possesses zones of different optical power to that of the rest of the lens.

The procedure used up to step d) is then the same as for the progressive lens, at least a plurality of images of the scrolling pattern being captured through the edged lens 10 synchronously with the scrolling, as described above. The statistical processing described above is applied to this plurality of images in order to determine the improved image of the edged lens 10.

The computer 160 is then programmed to identify, in the obtained improved image, an outline of the one or more zones of different optical power to that of the rest of the ophthalmic lens of the bi or trifocal lens. The position of this or these zones is then the optical characteristic determined in step d).

Furthermore, generally, it is possible to identify in the improved image IA the measured outline 20 of the edged lens 10 or defects in coating(s) of this edged lens 10.

The identification of the measured outline 20 of the edged lens 10 in the improved image optionally allows the geometric characteristic determined in step b) to be complemented.

In the case where the measured outline 20 has already been determined in step c), this identification in the improved image IA allows the measured outline determined in step b) to be confirmed and optionally made more precise.

Specifically, for certain edged lenses it is either difficult to determine the outline of the lens on the basis of the image captured in step b) or the determined outline is imprecise. This is for example the case for ophthalmic lenses with a polished mirror-like finish.

In the case where the geometric characteristics determined in step c) do not comprise the measured outline 20, the latter is determined on the basis of the improved image.

It is also possible to envision, as a variant of the steps b) and c) described above, that they be carried out with step d). In this case, no image without displayed pattern is captured. In step b), the image-capturing device captures the images of the scrolling pattern. During the implementation of steps c) and d), the improved image is determined on the basis of the captured images, and the geometric and optical characteristics of the edged lens are determined on the basis of this image. In particular, the image of the measured outline of the edged lens is identified in this improved image and the measured outline is deduced therefrom. The measured optical characteristics of the edged lens are determined on the basis of the identification, in the improved image, of images of micro-engravings of the edged lens.

Whatever the type of lens in question, the identification of coating defects allows the quality of the edged lens to be controlled. Depending on the central or peripheral position of the defects, the computer may be programmed to emit a warning signal indicating that the lens must be remanufactured.

Whatever the type of lens in question, for gradient-tinted edged ophthalmic lenses, in addition to the axis of the prescription of the lens, the axis of the gradient of the tint of the ophthalmic lens may also be determined. To this end, the axis of the direction of variation of brightness is determined in the image of the lens recorded in step b) or step d).

Similarly, for polarized edged ophthalmic lenses, the axis of the polarization is also checked.

This may for example be done using the polarization of the LCD screen of the displaying device 130. The edged lens 10 is rotated on or with the holder 110 until the light intensity passing through the ophthalmic lens is close to 0, this meaning that the axis of the polarization of the edged lens is orthogonal to the known axis of the polarization of the LCD screen.

The holder of the lens may be motorized in order to make the lens turn or indeed the lens may be turned manually by the operator. The axis of the polarization is determined by interpolating measurements carried out in the various positions of the edged lens.

In step e) it is a question in practice of checking the prescription of the lens-monocular pupillary distance, height and axis (axis of the cylinder, of the tint gradient and/or of the polarization) of the edged lens-against the prescription of the wearer. To this end, any errors in the centrality and/or axis of the edged lens 10 are determined.

In step c) the geometric characteristics of the edged lens 10, here its outline, were determined, and the optical characteristics of this edged lens were determined in step d), in the coordinate system of the image captured by the image-capturing device.

Whatever the type of edged lens 10, the computer is programmed to compare the measured geometric characteristic and the measured optical characteristic of the edged lens to a predetermined desired ophthalmic-lens model, comprising at least one desired geometric characteristic and one desired optical characteristic corresponding to said measured geometric characteristic and measured optical characteristic.

This model represents the desired lens.

Said desired ophthalmic-lens model is determined depending on the geometric and optical characteristics desired for the edged lens 10 contained in the file which the computer 160 accesses on the basis of the "job ticket".

Figure 2:
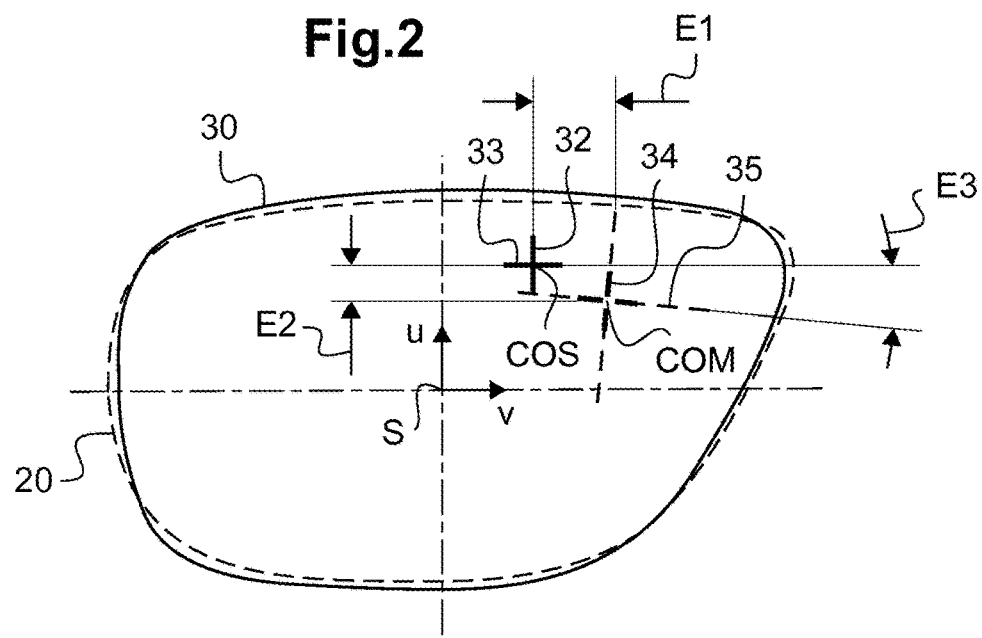

This model, one example of which is shown in FIG. 2 by the solid line, for example comprises the desired outline 30 for the lens, with the desired optical center COS in its desired position with respect to the desired outline 30, and the orientation of the optical axes 32, 33 of the desired lens with respect to the desired outline 30.

This model also optionally comprises a direction desired for the tint gradient of the lens and/or a direction desired for the polarization of this edged lens.

Generally, in step e), the computer 160 is programmed to make the one or more measured geometric characteristics correspond with their corresponding desired geometric characteristic. In this way, the desired and edged lenses may be positioned, with respect to each other, so as to be superposed as best as possible.

More precisely, here, in step e), the computer 160 is programmed to carry out the following substeps:

e1) a substep in which the measured outline is superposed on the desired outline by minimizing the discrepancy therebetween, e2) a substep in which the discrepancy between the measured optical characteristic and the desired optical characteristic is determined depending on the superposition obtained in step e1).

Step e1) allows the measured and desired optical characteristics to be placed back in the same edged-lens-related geometric coordinate system, this being shown in FIG. 2.

An algorithm for superposing the desired outline 20 and the measured outline 30 is described below.

The desired outline 20 and measured outline 30 are two closed outlines in 2 dimensions consisting of n points of coordinates (x, y) in a coordinate system associated with each desired outline 20 and measured outline 30, the origin of which (0, 0) is located in the interior of this outline.

The aim is to find the values of the translations Tx and Ty and rotation Rz to be applied to the measured outline 30 to make the errors between the desired outline 20 and the measured outline 30 having undergone these translations and rotations as small as possible.

The computer is programmed to calculate the center of gravity of each of the two outlines, denoted Cdg1 and Cdg2 below.

The center of gravity of each of the desired outline 20 and measured outline 30 may be calculated by finding the centroid of the triangles formed by the n points the common vertex of which is the coordinate (0, 0) of the origin of the coordinate system associated with the outline.

Each center of gravity is then determined using the formula:

$$Cdg = \begin{cases} \dfrac{\sum\limits_{i=1}^{n} \dfrac{(x_i + x_{i+1})}{3} \cdot S_i}{\sum\limits_{i=1}^{n} S_i} \\ \dfrac{\sum\limits_{i=1}^{n} \dfrac{(y_i + y_{i+1})}{3} \cdot S_i}{\sum\limits_{i=1}^{n} S_i} \end{cases}$$

where: $S_i = \dfrac{\sqrt{x_i \cdot y_{i+1} - y_i \cdot x_{i+1}}}{2}$ for $i = 1$ to $n$.

The computer is then programmed to recalculate the measured and desired outlines of the lens in a coordinate system centered on their respective centers of gravity Cdg1, Cdg2.

It is therefore a question of subtracting from the coordinates of each point of the desired outline 30 and measured outline 20 the coordinates of the corresponding center of gravity Cdg1, Cdg2.

It is then possible to superpose the centers of gravity Cdg1, Cdg2 of the two desired and measured outlines in order to superpose the two desired and measured outlines. The values of the translations Tx and Ty may be deduced from the discrepancy between the coordinates of the two determined centers of gravity.

Next, with an algorithm an example of which is given below, the rotation to be applied to the measured outline 20 in order to superpose it on the desired outline 30 is determined iteratively.

According to one example of this algorithm, the discrepancy between the measured outline 20 and the desired outline 30 is quantified by summing the distances between the two outlines for a predetermined number of angles distributed around the common center of gravity of the two outlines.

The number of angles is related to the desired resolution, and for example is lower than or equal to the number of points comprised in the corresponding outline. It is also possible to set an angular step size, for example equal to one tenth of a degree of angle, between two angles for which the discrepancy between the outlines is evaluated and to evaluate this discrepancy by interpolation between the closest points of the outlines for the corresponding set angles.

The discrepancy between the desired outline 30 and the measured outline 20 is thus determined for various values of the angle of rotation transforming the measured outline 20, and compared to a discrepancy threshold value.

When the calculated discrepancy is smaller than said discrepancy threshold value, the corresponding angle of rotation is used to transform the measured outline 20.

More precisely, for example, the rotations are considered to have as center the common center of gravity Cdg1, Cdg2 of the two outlines, the angle of rotation Rz is considered to be comprised between a minimum value and a maximum value, for example comprised between −Pi and Pi, and the value of the angle of rotation increment is successively decreased.

This increment value is for example initially equal to Pi/8. The increment for the following iteration is decreased, for example divided by two or by a higher integer.

Provided that the value of the increment remains higher than the desired precision in the angle of rotation, the computer calculates, for each angle of rotation Rz equal to the minimum value of the angle of rotation plus an integer number k times the angle increment, the discrepancy between the desired outline and the measured outline transformed by this rotation.

When this discrepancy drops below the discrepancy threshold value, the value of the angle of rotation Rz is determined as being the value of the angle of rotation tested in this iteration.

It is also possible to make provision for successive iterations to seek the minimum value of the discrepancy between the two outlines, then, in the following iteration, to re-center the maximum and minimum values of the tested angles of rotation on the value of the angle of rotation for which the discrepancy was found to be minimal. The increment for the following iteration is decreased, for example divided by two or by a higher integer.

The desired outline 20 and measured outline 30 then being superposed as best as possible, it is possible to determine the discrepancy between the desired optical center COS and the measured optical center COM.

These discrepancies are for example determined in a boxing-system coordinate system (S, U, V) corresponding to the boxing-system coordinate system of the desired outline 30. The center S of this coordinate system is the geometric center of the boxing-system rectangle in which the desired outline 30 is inscribed, and is called the boxing center. The axes of this boxing-system frame of reference are parallel to the sides of this rectangle.

The discrepancy between the desired optical center COS and the measured optical center COM thus allows the error in the monocular pupillary distance E1 and the error in the height E2 of the optical center with respect to the lower edge of the edged lens to be determined (FIG. 2).

The error in the monocular pupillary distance E1 is the coordinate along the axis U parallel to the smallest side of the boxing-system rectangle and the error in the height E2 of the optical center with respect to the lower edge of the edged lens is the coordinate along the axis V parallel to the largest side of the boxing-system rectangle (FIG. 2).

The angular discrepancy between the axis 32, 33 of the desired lens and the axis 34, 35 of the measured lens gives access to an axis error E3 of the edged lens (FIG. 2).

Similarly, the computer 160 compares the measured axis of the direction of the brightness variation to the axis desired for the brightness variation. The axis error in the tint gradient may be defined as the difference between the measured axis of the direction of the brightness variation and the desired axis.

For polarized edged ophthalmic lenses, the computer 160 compares the direction of the axis of the measured polarization to the axis direction desired for the polarization of the edged lens 10. The axis error in the polarization may be defined as the angle between the measured direction of the axis of the polarization and the desired direction of the axis of the polarization.

Thus, in a step f), the computer 160 determines, depending on the comparison made in step e), a parameter relating to the discrepancy between said measured outline and said desired outline and a parameter relating to the discrepancy between said measured optical characteristic and said desired optical characteristic.

This parameter relating to the discrepancy between said measured optical characteristic and said desired optical characteristic is here for example the determined value of the error between each measured optical characteristic and the corresponding desired optical characteristic.

The parameter relating to the discrepancy between said measured outline 20 and said desired outline 30 is for example the sum of the distances between the points of the measured outline 20 and of the desired outline 30 when the two outlines are superposed.

In step f), the computer 160 is then programmed to compare said parameter relating to the discrepancy between said measured outline 20 and said desired outline 30 and each parameter relating to the discrepancy between said measured optical characteristic and said desired optical characteristic to tolerance threshold values and to determine, depending on this comparison, an indicator of the conformity of the edged ophthalmic lens 10.

In practice here, the computer is then programmed to compare the errors to tolerated maximum error values. The parameter relating to the discrepancy between the desired outline and the measured outline is compared to a maximum threshold value tolerated for this parameter.

The indicator of the conformity of the edged lens 10 with respect to the desired optical characteristics is deduced therefrom.

When the determined errors and the parameter relating to the discrepancy between the desired outline 20 and the measured outline 30 are smaller than the aforementioned maximum error values and the tolerated maximum threshold value, the corresponding edged lens is declared to conform to the desired lens. The indicator indicates that the edged lens is compliant.

The tolerated maximum error values may advantageously be modulated depending on the desired optical characteristics of the lens and of standards in the countries in which the pair of spectacles will be used.

Preferably, the conformity of each lens is determined independently for the right lens and the left lens that are intended for a given frame.

Then, in a step g), the computer 160 determines, depending on the comparison made in step e), a parameter relating to the discrepancy between said measured optical characteristics for a right lens and a left lens that are intended for said frame.

The computer 160 then compares said parameter relating to the discrepancy between said measured optical characteristics, for a right lens and a left lens that are intended for said frame, to a tolerance threshold value and, depending on this comparison, an indicator of the conformity of the right and left edged ophthalmic lenses is determined.

Therefore, here, the errors described above are determined for each of the two, left and right, lenses intended to be mounted in a given frame, and then these errors are compared with one another.

The difference between the errors determined for the right and left lenses is compared to the corresponding tolerance threshold value. The conformity indicator indicates that the right and left lenses are compliant one with respect to the other if the difference between these errors remains below the corresponding tolerance threshold value.

Advantageously, it is also possible to deduce from the above the corresponding overall errors when the two, right and left, edged lenses are used in the associated frame. For example, an error in the total interpupillary distance, a difference in height between the right and left edged lenses, and an axial discrepancy between the right edged lens and the left edged lens are determined.

When the determined errors and the parameter relating to the discrepancy between the desired outline 20 and the measured outline 30 are larger than the aforementioned maximum error values and the tolerated maximum threshold value, the corresponding edged lens 10 is declared not to conform to the desired lens. The indicator indicates that the edged lens is not compliant.

The results, i.e. the error and conformity of the lens, may be recorded in the database 170 for archiving and/or analysis.

In the case where the edged lens 10 is declared not to conform, the device 100 may for example resend an order for this edged lens to be manufactured.

In the case where the edged lens 10 is declared to conform, it is for example sent to the customer accompanied by a quality-control certificate.

In case of return of an edged lens by an unsatisfied customer, the latter is checked with the device 100 and the results of this quality control are compared to those obtained before the edged lenses were sent to the customer.

Checking, with the device 100 and the method described here, an identical predetermined manufactured edged lens 10 at regular intervals on a production line furthermore makes it possible to check that edging tools, upstream of the checking device, contain no faults or have not become worn.

If a device 100 equipped with a suitable holder is used to fasten the frame equipped with its two ophthalmic lenses, it is also possible to directly check interpupillary distance, the heights of the optical centers with respect to the lower edge of the corresponding lens, and the axes of the edged ophthalmic lenses mounted in the frame.

Here, we have described the case where the desired and measured outlines are positioned, one with respect to the other, by minimizing the discrepancy between the two outlines, the discrepancy between the optical characteristics then being quantified on the basis of this relative position of the desired and measured outlines. As a variant, it is possible to envision positioning the desired and measured outlines of the edged lens one with respect to the other by minimizing the discrepancy between the desired and measured optical characteristics, for example by minimizing the distance between the desired and measured optical center and by minimizing the angular discrepancy between the desired and measured cylinder axis. The discrepancy between the desired and measured outlines is then quantified on the basis of this relative position.

The invention claimed is:

1. A method for checking at least one geometric characteristic and one optical characteristic of an edged ophthalmic lens, the method comprising the following steps:
  a) placing the edged ophthalmic lens on a holder;
  b) capturing at least one image of the edged ophthalmic lens;
  c) measuring, based on the captured image, a measured geometric characteristic of said edged ophthalmic lens;
  d) measuring at least one measured optical characteristic of the edged ophthalmic lens in a coordinate system of the image captured in step b);
  e) comparing said measured geometric characteristic associated with the measured optical characteristic to a predetermined desired ophthalmic-lens model that comprises at least one corresponding desired geometric characteristic and one corresponding desired optical characteristic; and
  f) determining and recording errors in one or more of an optical center and an optical axis of the edged ophthalmic lens based on the comparison of the measured geometric characteristic and the predetermined desired ophthalmic-lens model.

2. The method as claimed in claim 1, wherein, in step c), said measured geometric characteristic is the measured outline of the edged ophthalmic lens, and
in step e), the desired ophthalmic-lens model comprises a desired outline.

3. The method as claimed in claim 2, wherein, in step d), said optical characteristic comprises the position of the optical center and/or the direction of an optical axis of the edged ophthalmic lens, and the following substeps are carried out:
d1) prior to step c), placing the edged ophthalmic lens in a lensmeter and making a mark on said edged ophthalmic lens, said mark indicating the optical center and/or the direction of said optical axis on said edged ophthalmic lens, and
d2) identifying the image of the mark in the image captured in step b).

4. The method as claimed in claim 2, wherein the holder of said edged ophthalmic lens is located between an image-capturing apparatus configured to capture the image of the edged ophthalmic lens in step b), and a device configured to display a stationary pattern, in step d), by virtue of said image-capturing device, an image of the stationary pattern being captured through the edged ophthalmic lens, said optical characteristic being determined depending on the image of the stationary pattern.

5. The method as claimed in claim 2, wherein the holder of said edged ophthalmic lens is located between an image-capturing apparatus configured to capture the image of the ophthalmic lens in step b), and a device configured to display a scrolling pattern, in step d), by virtue of said image-capturing device, a plurality of images of the scrolling pattern being captured through the edged ophthalmic lens, said optical characteristic being determined depending on the plurality of images.

6. The method as claimed in claim 2, wherein, in step c), said measured geometric characteristic is the measured outline of the edged lens, and
in step e), the desired ophthalmic-lens model comprises a desired outline, and
the following substeps are carried out:
e1) superposing the measured outline on the desired outline by minimizing the discrepancy therebetween, and
e2) determining the discrepancy between the measured optical characteristic and the desired optical characteristic depending on the superposition obtained in step e1).

7. The method as claimed in claim 1, wherein, in step d), said optical characteristic comprises the position of the optical center and/or the direction of an optical axis of the edged ophthalmic lens, and the following substeps are carried out:
d1) prior to step c), placing the edged ophthalmic lens in a lensmeter and making a mark on said edged ophthalmic lens, said mark indicating the optical center and/or the direction of said optical axis on said edged ophthalmic lens, and
d2) identifying the image of the mark in the image captured in step b).

8. The method as claimed in claim 1, wherein the holder of said edged ophthalmic lens is located between an image-capturing apparatus configured to capture the image of the edged ophthalmic lens in step b), and a device configured to display a stationary pattern, in step d), by virtue of said image-capturing device, an image of the stationary pattern being captured through the edged ophthalmic lens, said optical characteristic being determined depending on the image of the stationary pattern.

9. The method as claimed in claim 1, wherein the holder of said edged ophthalmic lens is located between an image-capturing apparatus configured to capture the image of the ophthalmic lens in step b), and a device configured to display a scrolling pattern, in step d), by virtue of said image-capturing device, a plurality of images of the scrolling pattern being captured through the edged ophthalmic lens, said optical characteristic being determined depending on the plurality of images.

10. The method as claimed in claim 9, wherein, in step d), the scrolling pattern displayed by the display device has a predetermined spatial period and said plurality of images comprise a number m of images, each capture of one image of said plurality of images by the image-capturing device corresponding to the display of the scrolling pattern shifted by a distance equal to 1/m times the spatial period of the scrolling pattern with respect to the preceding capture.

11. The method as claimed in claim 10, wherein, in step d), determining an improved image of said edged ophthalmic lens by applying statistical processing to said plurality of images of the scrolling pattern through the edged ophthalmic lens.

12. The method as claimed in claim 11, wherein, in step d), in said improved image of said edged ophthalmic lens, the image of at least one of the following elements is identified:
engravings produced on the surface of the edged ophthalmic lens or in the volume of the edged ophthalmic lens,
a measured outline of the edged ophthalmic lens,
an outline of a zone of different optical power to optical power of the rest of the edged ophthalmic lens, and
defects in the coating(s) of the edged ophthalmic lens.

13. The method as claimed in claim 1, wherein, in step c), said measured geometric characteristic is the measured outline of the edged lens, and
in step e), the desired ophthalmic-lens model comprises a desired outline, and
the following substeps are carried out:
e1) superposing the measured outline on the desired outline by minimizing the discrepancy therebetween, and
e2) determining the discrepancy between the measured optical characteristic and the desired optical characteristic depending on the superposition obtained in step e1).

14. The method as claimed in claim 1, wherein, in step d), said measured optical characteristic of the edged ophthalmic lens comprises at least one of the following characteristics:
a position of the optical center,
a direction of the optical axis,
a measured direction of a tint gradient of the edged ophthalmic lens, and
a measured direction of a polarization axis of the edged ophthalmic lens.

15. The method as claimed in claim 1, wherein, in the step f), determining a parameter relating to the discrepancy between said measured geometric characteristic and said desired geometric characteristic and a parameter relating to the discrepancy between said measured optical characteristic and said desired optical characteristic, depending on the comparison made in step e), in order to determine the errors in one or more of the optical center and the optical axis of the edged ophthalmic lens.

16. The method as claimed in claim 15, wherein, in the step f), comparing said parameter relating to the discrepancy between said measured geometric characteristic and said desired geometric characteristic and said parameter relating to the discrepancy between said measured optical characteristic and said desired optical characteristic to tolerance threshold values, and determining an indicator of the conformity of the edged ophthalmic lens depending on the comparison to determine the errors in one or more of the optical center and the optical axis of the edged ophthalmic lens.

17. The method as claimed in claim 1, wherein, in a step g), depending on the comparison made in step e), determining a parameter relating to the discrepancy between said measured optical characteristics for a right lens and a left lens that are intended for said frame.

18. The method as claimed in the claim 17, wherein, in step g), comparing said parameter relating to the discrepancy between said measured optical characteristics, for a right lens and a left lens that are intended for said frame, to a tolerance threshold value, and determining an indicator of the conformity of the right and left edged ophthalmic lenses, depending on the comparison.

19. A device for checking at least one geometric and/or optical characteristic of an edged ophthalmic lens comprising:

a holder for said edged lens;
    an image-capturing device on one side of the holder;
    a displaying device configured to display at least one scrolling pattern and to make the scrolling pattern scroll in at least one predetermined scrolling direction with respect to said holder; and
    a computer configured to:
        synchronize a plurality of captures of images by the image-capturing device and the scrolling of the scrolling pattern performed by the displaying device, and
        determine said geometric and/or optical characteristic of the edged ophthalmic lens depending on the plurality of captured images, compare the geometric and/or optical characteristic with a corresponding desired characteristic, determine and record errors in one or more of an optical center and an optical axis of the edged ophthalmic lens based on the comparison of the geometric and/or optical characteristic and the predetermined desired characteristic.

20. The device as claimed in the claim 19, wherein said scrolling pattern comprises alternating black and white strips, and wherein the image-capturing device is focused in proximity to the holder, at distance from said scrolling pattern.

* * * * *